(12) United States Patent
Rietzel

(10) Patent No.: US 7,682,078 B2
(45) Date of Patent: Mar. 23, 2010

(54) METHOD FOR DETERMINING A RANGE OF RADIATION

(75) Inventor: Eike Rietzel, Darmstadt (DE)

(73) Assignee: Siemens Aktiengesellschaft, Munich (DE)

(*) Notice: Subject to any disclaimer, the term of this patent is extended or adjusted under 35 U.S.C. 154(b) by 0 days.

(21) Appl. No.: 11/973,479

(22) Filed: Oct. 9, 2007

(65) Prior Publication Data

US 2008/0089464 A1  Apr. 17, 2008

(30) Foreign Application Priority Data

Oct. 12, 2006 (DE) ............. 10 2006 048 426

(51) Int. Cl.
*G01D 18/00* (2006.01)
(52) U.S. Cl. .................. 378/207; 378/65
(58) Field of Classification Search ........... 378/64, 378/65, 163–165, 207, 210
See application file for complete search history.

(56) References Cited

U.S. PATENT DOCUMENTS

| 5,673,303 | A | 9/1997 | Hangartner |
| 5,727,041 | A | 3/1998 | Hsieh |
| 6,148,272 | A * | 11/2000 | Bergstrom et al. .......... 702/179 |
| 6,215,841 | B1 | 4/2001 | Hsieh |
| 7,257,191 | B2 | 8/2007 | Sommer |
| 2003/0219098 | A1 | 11/2003 | McNutt et al. |
| 2005/0192764 | A1 | 9/2005 | Holland |
| 2007/0049839 | A1 | 3/2007 | Odry et al. |

FOREIGN PATENT DOCUMENTS

DE   10 2004 057 726 A1   6/2006

OTHER PUBLICATIONS

European Search Report for EP 07 11 6397 dated Dec. 21, 2007.
German Office Action dated Aug. 31, 2007 with English translation of pertinent portions.
Beispielsweise, S.: "Medizinische Informatik, Biometrie und Epidemiologie," hrsg. Von Hans-Jürgen Seelos, Walter de Gruyter & Co., Berlin, 1997, S. 71.
Jäkel O., et al., "Relation Between Carbon Ion Ranges and X-ray CT Numbers," DLFZ Heidelberg, Received Jan. 2001, accepted for publication Jan. 25, 2001, pp. 701-703.
Kanematsu et al., "A CT Calibration Method Based on the Polybinary Tissue Model for Radiotherapy Treatment Planning," Institute of Physics Publishing, Phys. Med. Biol. 48 (2003), pp. 1053-1064.
Matsufuji et al., "Relationship Between CT Number and Electron Density, Scatter Angle and Nuclear Reaction for Hadron-Therapy Treatment Planning," Institute of Physics Publishing, Phys. Med. Biol. 48 (1998), pp. 3261-3275.

(Continued)

*Primary Examiner*—Jurie Yun
(74) *Attorney, Agent, or Firm*—Brinks, Hofer, Gilson & Lione

(57) ABSTRACT

A method for determining a range of radiation is provided. The method includes defining a target volume to be irradiated using a plurality of voxels; determining, without exposing the target volume to radiation, radiation-attenuating properties that are associated with individual voxels of the plurality of voxels; deriving a range datum from the radiation-attenuating properties; and changing the range datum of a first voxel if the range datum of the first voxel differs from the range datum of two adjacent voxels.

17 Claims, 1 Drawing Sheet

OTHER PUBLICATIONS

Schaffner et al., "The Precision of Proton Range Calculations in Proton Radiotherapy Treatment Planning: Experimental Verification of the Relation Between CT-HU and Proton Stopping Power," Institute of Physics Publishing, Phys. Med. Biol. 43 (1998), pp. 1579-1592.

Schneider et al., "The Calibration of CT Hounsfield Units for Radiotherapy Treatment Planning," Phys. Med. Biol. 41 (1996), IOP Publishing Ltd., pp. 111-124.

Schneider et al., "Patient Specific Optimization of the Relation Between CT—Hounsfield Units and Proton Stopping Power with Proton Radiography," Med. Phys. 32(1), Jan. 2005, pp. 195-199.

* cited by examiner

METHOD FOR DETERMINING A RANGE OF RADIATION

The present patent document claims the benefit of the filing date of DE 10 2006 048 426.6, filed Oct. 12, 1006, which is hereby incorporated by reference.

BACKGROUND

The present embodiments relate to a method for determining the range (path length or depth) of radiation, and to an apparatus that determines the range of radiation.

"Relation between carbon ion ranges and x-ray CT numbers" (O. Jäkel, C. Jacob, D. Schardt, C. P. Karger, G. H. Hartmann; Medical Physics, Vol. 28, No. 4, April 2001, pp. 701-703) addresses the range of particle radiation in various phantom materials and in bone. Various types of tissue, including muscles, fat and lungs, were simulated with phantom materials. Range measurements were performed with the aid of an absorber. The absorber contains water in a variable layer thickness. The absorber, in addition to the phantom material, was positioned between two ionization chambers. The irradiation was perpendicular to the ionization chambers used for the charge measurement. A relationship was ascertained in various materials between the attenuation of X-radiation, which can be determined by computer tomography, and the range of particles, such as carbon ions and protons.

German Patent Disclosure DE 10 2004 057 726 A1 discloses a medical examination and treatment system. The examination and treatment system includes a radiation source that emits particle radiation, such as ion radiation. The examination and treatment system has both an X-ray emitter, disposed on the side of the target volume opposite the radiation source, and a detector. The purpose is to enable both time-saving scanning and precise radiation therapy. The irradiation profile of the particle beam may be monitored. However, determining the range of the particle radiation is not the subject of DE 10 2004 057 726 A1.

In particle-beam therapy, it is important that the range of the radiation used in the target volume be predicted as precisely as possible. Unlike electromagnetic radiation, particle radiation has an inverted dosage profile. The radiation dose deposited in the target volume exposed to the radiation increases with increasing penetration depth, and it reaches a sharp maximum point just before the maximum range. The inverted dosage profile spares the tissue located in the beam path ahead of the target volume to be treated. Optimal radiation planning demands that the location of the maximum point of the dosage profile be known precisely.

SUMMARY

The present embodiments may obviate one or more limitations or drawbacks inherent in the related art. For example, in one embodiment, a range of radiation, such as particle radiation, in a target volume that is not homogeneous with regard to radiation-affecting properties is precisely determined.

In one embodiment, the range of radiation, such as particle radiation, is determined based on breaking down (characterizing) a target volume to be irradiated into a plurality of volume elements. The plurality of volume elements may be called voxels. The individual voxels may, for example, be block-shaped. Alternatively, non-block-shaped voxels may have non-uniform size.

The classification into volume elements is used first to obtain information with local resolution about radiation-attenuating properties of the target volume. The information is obtained, for example, by radiology, computed tomography, or some other way. The target volume is not exposed to the radiation whose range is to be determined to obtain this information. The radiation-attenuating properties of each voxel examined are preferably classified in Hounsfield units (see for instance "*Medizinische Informatik, Biometrie und Epidemologie*" [Medical Information Processing, Biometrics, and Epidemiology], edited by Hans-Jürgen Seelos, Walter de Gruyter & Co., Berlin, 1997, page 71). The range of values of the Hounsfield units (HU) is from −1000 (extremely slight attenuation of X-radiation) to +2000 (very strong attenuation of X-radiation), for example. The value for water is set by definition at 0.

Radiation-attenuating properties ascertained for the individual voxels are used to derive a range datum that refers to the range of that particular radiation, such as particle radiation, with which the target volume is to be treated at some later time. The range datum may be determined as a water-equivalent range (WEPL, water equivalent path length). The association of range datum with radiation-attenuating properties is based, for example, on data obtained beforehand experimentally and/or theoretically (see e.g., the article by Jäkel et al. cited above). The relationship between radiation-attenuating properties, expressed in Hounsfield units, and water-equivalent ranges, referred to a certain radiation, may be stored in table form, for example, as a calibration curve.

The range datum of the first voxel is not changed if the range datum obtained for a first voxel is identical to the range datum of the surrounding voxels. However, the range datum of the first voxel is changed if the range datum of the first voxel does differ from the range datum of two voxels adjacent to the first voxel in different ways. The changed associations between radiation-attenuating properties and the range datum, taken together, form a second calibration curve. This second calibration curve can either be stored in its entirety in memory, like the first calibration curve, or it may be generated as needed for individual values from the first calibration curve.

In one embodiment, the water-equivalent range associated with the first voxel is corrected, if a lesser water-equivalent range for a first adjacent voxel and a higher water-equivalent range, in comparison to the first voxel, for a second adjacent voxel have been determined. The adjacent voxels are disposed on opposite sides of the first voxel.

A partial volume effect may exists if the water-equivalent range determined for one voxel is located between values that have been ascertained for voxels adjacent to that voxel. For example, a partial volume effect may exists whenever a very low value on the Hounsfield scale has been assigned to one of the adjacent voxels, and a very high value on this scale has been assigned to the further adjacent voxel. The low value on the Hounsfield scale then corresponds to a low value for the water-equivalent range, while the very high value on the Hounsfield scale is expressed by a high value of the water-equivalent range. The term partial volume effect may refer to material properties that are between the properties of the voxels opposite one another and adjacent to the middle voxel being assigned to the middle voxel.

In the voxel where the partial volume effect occurs, there is no third substance whose properties are between the properties of the substances that fill up the adjacent voxels. There is only a boundary face between the substances detected in the adjacent voxels. If the adjacent voxels were not included in the evaluation, the result would be a misinterpretation of the radiation-attenuating properties assigned to the middle voxel. As a result of this misinterpretation, a voxel through which a boundary face extends would be assigned an incorrect, for example, overly high, water-equivalent range.

To avoid this kind of misinterpretation, according to the method of the invention, in the association, also called calibration between radiation-attenuating properties detected per voxel and water-equivalent ranges, the surroundings of the voxel to be calibrated is taken into account as well. Algorithms that are used in image processing may be used to include data from surrounding voxels in calibrating the Hounsfield units in terms of water equivalence. Adaptive filtering is one example that uses the surroundings within a certain mask to define the filter outcome.

Boundary face effects may be taken into account because, during the calibration necessary to prepare for the irradiation, the calibration data used for a particular voxel is dependent on measurement data determined for this voxel and on measurement data, such as computed tomography data, of adjacent voxels. Insufficient and excessive ranges that would lead to incorrect dosages, such as underdosage in the target volume and overdosage in the surrounding tissue, are avoided. The calibration data made for individual voxels may be corrected depending on their respective surroundings. This correction can in an individual case vary the particle range by an amount that is greater than the length, measured in the radiation direction, of one voxel. As a comparison situation, the assumption here is a radiation treatment based on a calibration which does take into account the different material properties detected for individual voxels, but does not make any corrections dependent on the surroundings.

High precision in particle therapy is attained, because to associate radiation-attenuating properties, measured with local resolution, with predicted water-equivalent ranges, a plurality of calibration curves are made available. An automatic selection of the suitable calibration curve is made based on a comparison of the measured radiation-attenuating properties of a volume element with the radiation-attenuating properties of surrounding volume elements.

DETAILED DESCRIPTION

Figure 1:
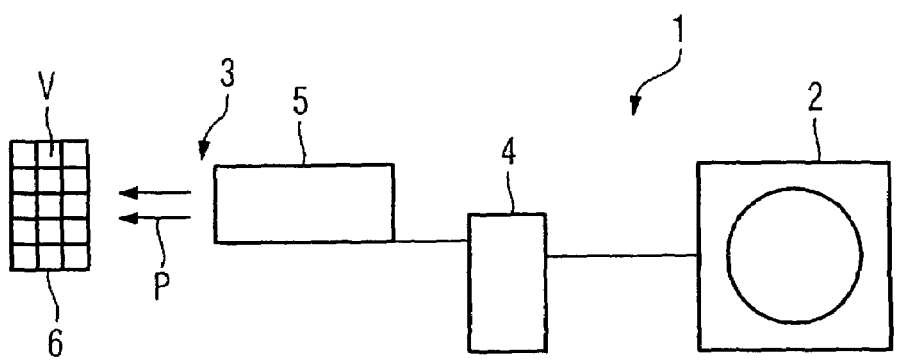
FIG. 1 illustrates one embodiment of a medical examination and treatment system.

In one embodiment, as shown in FIG. 1, a medical examination and treatment system 1 includes a diagnostic device 2, such as a computed tomography scanner, a radiation treatment system as its therapy device 3, and a computation unit 4. The computation unit (computer or processor) 4 links the diagnostic device 2 with the therapy device 3. Alternatively, the computation unit 4 may be a relatively large data processing network, for example, integrated with a radiology information system and/or hospital information system. The radiation treatment system 3 includes a radiation source 5, which emits particle radiation P, for example, carbon-ion radiation, which strikes a target volume 6 to be treated. The target volume 6 is subdivided into many block-shaped voxels V using a Cartesian coordinate system. The range of the particle radiation P in the target volume 6 is determined with the aid of the computation unit 4. The computation unit 4 is arranged in terms of programming for performing the method described hereinafter.

The patient who is to be irradiated using the therapy device 3 is first examined by the diagnostic device 2. The diagnostic device 2 may perform an imaging medical procedure. In this procedure a volume data set is acquired, and within a certain volume, such as the volume designed as the target volume 6 for later irradiation, each voxel V is assigned a gray value that indicates the attenuation of the X-radiation in the applicable voxel V. The attenuation of the X-radiation provides density information. The attenuation is expressed in Hounsfield units (HU).

From the attenuation, indicated in Hounsfield units, of the X-radiation and utilizing empirical data found, for example, in "Hounsfield look-up tables," a value is first ascertained separately for each voxel V. The value indicates the water-equivalent range (WEPL) of the particle radiation P. If the tissue to be irradiated, such as the target volume 6, were completely homogeneous, then the range of the particle radiation P could be determined directly from the value of the water-equivalent range (WEPL).

Figure 2:
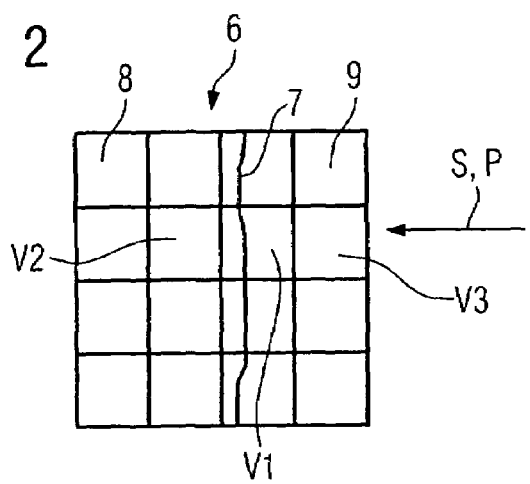
FIG. 2 illustrates a section through the target volume treated by the examination and treatment system of FIG. 1.

The target volume 6 may include nonhomogeneities. Practically every target volume 6 includes nonhomogeneieties. This kind of more-complex situation in irradiating the target volume 6 with the particle radiation P, of which a single beam S is indicated, is sketched in FIG. 2. The target volume 6 includes a surface 7 that forms the boundary face between a first partial volume 8, on the left of the surface 7 in FIG. 2, and a second partial volume 9. The first partial volume 8 may be bone and the second partial volume 9 may be air. The beam S passes through both air and bone. The beam S strikes the surface 7 of the bone in the first voxel V1. In FIG. 2, the first voxel V1 is bounded (surrounded) on opposite sides, on the left and right, respectively, of the voxel V1, by a second voxel V2, located entirely inside the bone, and a third voxel V3, located entirely outside the bone. In the exemplary embodiment, all the voxels V, V1, V2, V3 are cubic in shape, with an edge length of 1 mm. A Hounsfield value of +1000, for example, is assigned to the second voxel V2, while a Hounsfield value of −1000 is assigned to the third voxel V3 that is located in the air. The Hounsfield value may be determined by computed tomography scanning. The Hounsfield value of the middle voxel V1, through which the boundary face 7 between the bone and air extends, is 0.

Figure 3:
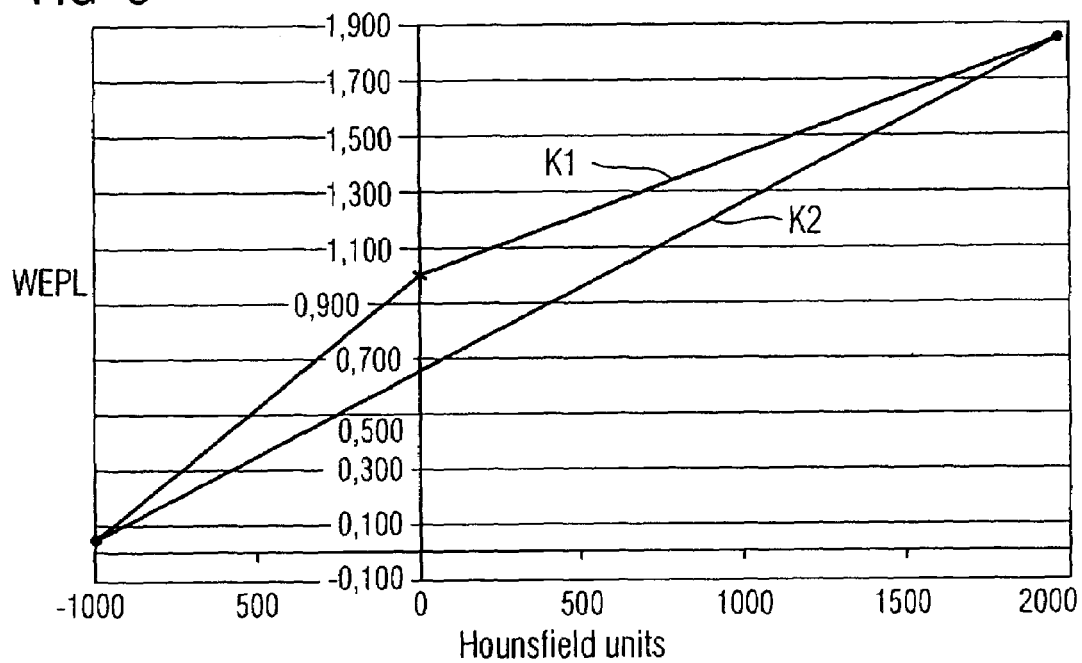
FIG. 3 is a graph showing one relationship between radiation-attenuating properties of the target volume that are ascertained by measurement and range data.

Each Hounsfield value may be assigned a water-equivalent range (WEPL). As shown in FIG. 3, the WEPL values may be used to generate a first calibration curve K1. The first calibration curve K1 may be stored in memory in the computation unit 4. The calibration curve K1 represents a relationship between the property of a material for attenuating X-radiation and the values of the water-equivalent range. The calibration curve K1 agrees with a curve shown in the above-cited publication by Jäkel et al (page 702, FIG. 2). According to the calibration curve K1, a WEPL value of 1 is to be associated with the Hounsfield value of 0.

The WEPL value of 1 corresponding to the Hounsfield value of 0 is correct by definition if the material being observed is water, and it may also be correct for some types of soft tissue. In the present case, in which there is neither water nor soft tissue in the voxel V1, however, assuming a WEPL of 1 for the voxel V1 would lead to radiation planning that only inadequately takes into account the actual composition of the target volume 6.

Under the given ambient conditions, for example, with a central voxel V1 that borders on a voxel V3 having a lower Hounsfield value and a voxel V2 with a higher Hounsfield value, a WEPL value of 0.7, or in other words a 30% lower WEPL value is correct, thus deviating from the first calibration curve K1. The corrected WEPL value is part of a second calibration curve K2, which may be automatically selected when the voxel V1 is identified as being located on a boundary face, in this case the surface 7. As a condition for the identification of a boundary face, a minimal difference between the radiation-attenuating properties of the central voxel V1 and the voxels V2, V3 adjacent to it on opposite sides, can preferably be defined, for example, being adjustable by software. The minimal difference can be expressed in Hounsfield units.

As shown in FIG. 3, the deviation between the calibration curves K1, K2, selected as a function of the surroundings, is greatest for the Hounsfield value of 0, while the calibration curves K1, K2 converge in the direction of Hounsfield values that are located further in the negative range and further in the positive range. In these ranges, no boundary faces exist between materials having extremely different radiation-attenuating properties or WEPL values that differ greatly from one another.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

The invention claimed is:

1. A method for determining a range of particle radiation, the method comprising:
    defining a target volume to be irradiated, the target volume characterized by a plurality of voxels;
    determining, without exposing the target volume to particle radiation, radiation-attenuating properties that are associated with individual voxels of the plurality of voxels by performing a medical imaging procedure;
    deriving a first range datum of a first voxel and range datums of two adjacent voxels from the radiation-attenuating properties; and
    changing the first range datum of the first voxel when the range datum of the first voxel differs from the range datums of the two adjacent voxels.

2. The method as defined by claim 1, wherein the determining the radiation-attenuating properties of the target volume includes using a radiology procedure.

3. The method as defined by claim 1, wherein determining the radiation-attenuating properties includes using a computed tomography procedure.

4. The method as defined by claim 1, wherein the radiation-attenuating properties are determined in Hounsfield units.

5. The method as defined by claim 1, wherein the range datum of the first voxel is a water-equivalent range.

6. The method as defined by claim 5, comprising: correcting the range datum of the first voxel whenever a lesser water-equivalent range has been determined for a first adjacent voxel and a higher water-equivalent range, in comparison to the first voxel, has been determined for a second adjacent voxel.

7. The method as defined by claim 6, wherein the first and second adjacent voxels that are adjacent to the first voxel and have a lesser or higher water-equivalent range are disposed on opposite sides of the first voxel.

8. The method as defined by claim 7, wherein correcting the range datum includes reducing the water-equivalent range associated with the first voxel.

9. The method as defined by claim 1, wherein the first voxel has a density that is different than densities of the two adjacent voxels.

10. The method as defined by claim 1, wherein changing the first range datum includes changing the first range datum of the first voxel when the range datum of the first voxel differs from the range datums of the two adjacent voxels in different ways.

11. The method as defined by claim 1, wherein changing includes determining whether the first range datum of the first voxel differs from the range datums of the two adjacent voxels.

12. An apparatus for determining a range of radiation, the apparatus comprising:
    a diagnostic device that is operable to obtain radiation-attenuating properties of a target volume; and
    a computation unit that is operable to derive a range datum from the radiation-attenuating properties of the target volume and change the range datum of a first voxel if the range datum of the first voxel differs from range datums of two adjacent voxels,
    wherein the first voxel and two adjacent voxels are voxels of the target volume.

13. The apparatus as defined by claim 12, wherein the radiation-attenuating properties of the target volume are derived using a radiology procedure.

14. The apparatus as defined by claim 9, wherein the radiation-attenuating properties of the target volume are derived using a computed tomography procedure.

15. The apparatus as defined by claim 12, wherein the range of radiation is a range of particle radiation.

16. The apparatus as defined by claim 12, wherein the range datum of the first voxel is a water-equivalent range, and wherein the computation unit is operable to correct the range datum of the first voxel whenever a lesser water-equivalent range has been determined for a first adjacent voxel and a higher water-equivalent range, in comparison to the first voxel, has been determined for a second adjacent voxel.

17. The apparatus as defined by claim 12, further comprising a therapy device that is controllable by the computational unit in accordance with changed range datum.

* * * * *